US012753209B2

(12) United States Patent
Lu et al.

(10) Patent No.: US 12,753,209 B2
(45) Date of Patent: Oct. 6, 2026

(54) ULTRASMALL GAS-FILLED PROTEIN NANOSTRUCTURES

(71) Applicant: William Marsh Rice University, Houston, TX (US)

(72) Inventors: Jiaozhi Lu, Houston, TX (US); Zongru Li, Nanjing (CN); Qionghua Shen, Houston, TX (US)

(73) Assignee: William Marsh Rice University

( * ) Notice: Subject to any disclaimer, the term of this patent is extended or adjusted under 35 U.S.C. 154(b) by 508 days.

(21) Appl. No.: 18/310,512

(22) Filed: May 1, 2023

(65) Prior Publication Data

US 2023/0348542 A1 Nov. 2, 2023

Related U.S. Application Data

(60) Provisional application No. 63/336,860, filed on Apr. 29, 2022.

(51) Int. Cl.

| | |
|---|---|
| ***A61K 39/00*** | (2006.01) |
| ***A61P 37/02*** | (2006.01) |
| ***B82Y 5/00*** | (2011.01) |
| ***C07K 14/195*** | (2006.01) |

(52) U.S. Cl.

CPC ............ *C07K 14/195* (2013.01); *A61P 37/02* (2018.01); *B82Y 5/00* (2013.01)

(58) Field of Classification Search

CPC combination set(s) only.
See application file for complete search history.

(56) References Cited

PUBLICATIONS

Ning et al Journal of Bacteriology (1998), 180(9), 2450-2458).*
Devos et al., (Proteins: Structure, Function and Genetics, 2000, vol. 41: 98-107).*
Whisstock et al., (Quarterly Reviews of Biophysics 2003, vol. 36 (3): 307-340,).*
Mikayama et al. (Nov. 1993. Proc.Natl.Acad.Sci. USA, vol. 90 : 10056-10060).*
Arvanitis, C.D., Ferraro, G.B., and Jain, R.K. (2020). The blood-brain barrier and blood-tumour barrier in brain tumours and metastases. Nature Reviews Cancer 20, 26-41.
Banks, W.A. (2016). From blood-brain barrier to blood-brain interface: new opportunities for CNS drug delivery. Nature Reviews Drug Discovery 15, 275-292.
Bar-On, Y.M., Flamholz, A., Phillips, R., and Milo, R. (2020). SARS-CoV-2 (COVID-19) by the numbers. eLife 9, e57309.
Bez, M., Foiret, J., Shapiro, G., Pelled, G., Ferrara, K.W., and Gazit, D. (2019). Nonviral ultrasound-mediated gene delivery in small and large animal models. Nat Protoc 14, 1015-1026.
Bez, M., Sheyn, D., Tawackoli, W., Avalos, P., Shapiro, G., Giaconi, J.C., Da, X., David, S.B., Gavrity, J., Awad, H.A., et al. (2017). In situ bone tissue engineering via ultrasound-mediated gene delivery to endogenous progenitor cells in mini-pigs. Sci Transl Med 9, eaal3128.
Chen, S., Ding, J.-h., Bekeredjian, R., Yang, B.-z., Shohet, R.V., Johnston, S.A., Hohmeier, H.E., Newgard, C.B., and Grayburn, P.A. (2006). Efficient gene delivery to pancreatic islets with ultrasonic microbubble destruction technology. Proc Natl Acad Sci U S A 103, 8469-8474.
Feffara, K., Pollard, R., and Borden, M. (2007). Ultrasound microbubble contrast agents: fundamentals and application to gene and drug delivery. Annu Rev Biomed Eng 9, 415-447.
Fujii, H., Li, S.-H., Wu, J., Miyagi, Y., Yau, T.M., Rakowski, H., Egashira, K., Guo, J., Weisel, R.D., and Li, R.-K. (2011). Repeated and targeted transfer of angiogenic plasmids into the infarcted rat heart via ultrasound targeted microbubble destruction enhances cardiac repair. Eur Heart J 32, 2075-2084.
Gaumet, M., Vargas, A., Gurny, R., and Delie, F. (2008). Nanoparticles for drug delivery: The need for precision in reporting particle size parameters. Eur J Pharm Biopharm 69, 1-9.
Ilovitsh, T., Feng, Y., Foiret, J., Kheirolomoom, A., Zhang, H., Ingham, E.S., Ilovitsh, A., Tumbale, S.K., Fite, B.Z., Wu, B., et al. (2020). Low-frequency ultrasound-mediated cytokine transfection enhances T cell recruitment at local and distant tumor sites. Proc Natl Acad Sci U S A 117, 12674-12685.
Irvine, D.J., and Dane, E.L. (2020). Enhancing cancer immunotherapy with nanomedicine. Nature Reviews Immunology 20, 321-334.
Jafari Sojahrood, A., de Leon, A.C., Lee, R., Cooley, M., Abenojar, E.C., Kolios, M.C., and Exner, A.A. (2021). Toward Precisely Controllable Acoustic Response of Shell-Stabilized Nanobubbles: High Yield and Narrow Dispersity. ACS Nano 15, 4901-4915.
Janib, S.M., Moses, A.S., and MacKay, J.A. (2010). Imaging and drug delivery using theranostic nanoparticles. Adv Drug Del Rev 62, 1052-1063.
Khestanova, E., Guinea, F., Fumagalli, L., Geim, A.K., and Grigorieva, I.V. (2016). Universal shape and pressure inside bubbles appearing in van der Waals heterostructures. Nature Communications 7, 12587.
Lakshmanan, A., Lu, G.J., Farhadi, A., Nety, S.P., Kunth, M., Lee-Gosselin, A., Maresca, D., Bourdeau, R.W., Yin, M., Yan, J., et al. (2017). Preparation of biogenic gas vesicle nanostructures for use as contrast agents for ultrasound and MRI. Nat Protoc 12, 2050-2080.
Li, Z., Shen, Q., Dai, Y., Anderson, A.P., Iburg, M., Lin, R., Zimmer, B., Meyer, M.D., You, L., Chilkoti, A., et al. (2023). Spatial organization of gas vesicles is governed by phase-separable GvpU. bioRxiv preprint.
Lindner, J.R. (2004). Microbubbles in medical imaging: current applications and future directions. Nature Reviews Drug Discovery 3, 527-533.

(Continued)

*Primary Examiner* — Jennifer E Graser
(74) *Attorney, Agent, or Firm* — Riverside Law LLP

(57) ABSTRACT

In one aspect, the present disclosure describes ultrasmall gas vesicle compositions comprising modified gas vesicle shell proteins. Also disclosed herein are polynucleotide sequences which encode such compositions. Methods of treatment comprising administering such gas vesicle compositions are also provided.

11 Claims, 3 Drawing Sheets
(3 of 3 Drawing Sheet(s) Filed in Color)
Specification includes a Sequence Listing.

(56) References Cited

PUBLICATIONS

Mitragotri, S. (2005). Healing sound: the use of ultrasound in drug delivery and other therapeutic applications. Nature Reviews Drug Discovery 4, 255-260.
Pfeifer, "Gas vesicles of Archaea and bacteria," *Complex Intracellular Structures in Prokaryotes*, 115-140, 2006.
Pfeifer, F. (2012). Distribution, formation and regulation of gas vesicles. Nat Rev Microbiol 10, 705-715.
Pfeifer, F. Recent Advances in the Study of Gas Vesicle Proteins and Application of Gas Vesicles in Biomedical Research. Life 2022, 12, 1455.
Sawyer, D.P., Bar-Zion, A., Farhadi, A., Shivaei, S., Ling, B., Lee-Gosselin, A., and Shapiro, M.G. (2021). Ultrasensitive ultrasound imaging of gene expression with signal unmixing. Nat Methods 18, 945-952.
Schudel, A., Francis, D.M., and Thomas, S.N. (2019). Material design for lymph node drug delivery. Nature Reviews Materials 4, 415-428.
Shimamura, M., Sato, N., Taniyama, Y., Yamamoto, S., Endoh, M., Kurinami, H., Aoki, M., Ogihara, T., Kaneda, Y., and Morishita, R. (2004). Development of efficient plasmid DNA transfer into adult rat central nervous system using microbubble-enhanced ultrasound. Gene Ther 11, 1532-1539.
Sirsi, S.R., and Borden, M.A. (2009). Microbubble compositions, properties and biomedical applications. Bubble Science, Engineering & Technology 1, 3-17.
Swartz, M.A. (2001). The physiology of the lymphatic system. Adv Drug Del Rev 50, 3-20.
Takeuchi, D., Sato, N., Shimamura, M., Kurinami, H., Takeda, S., Shinohara, M., Suzuki, S., Kojima, M., Ogihara, T., and Morishita, R. (2008). Alleviation of Aβ-induced cognitive impairment by ultrasound-mediated gene transfer of HGF in a mouse model. Gene Ther 15, 561-571.
Terstappen, G.C., Meyer, A.H., Bell, R.D., and Zhang, W. (2021). Strategies for delivering therapeutics across the blood-brain barrier. Nature Reviews Drug Discovery 20, 362-383.
Van Keulen et al, "Gas vesicles in actinomycetes: old buoys in novel habitats?," *Trends Microbiol*. 13(8):350-354, 2005.
Walsby, A.E., Revsbech, N.P., and Griffel, D.H. (1992). The gas permeability coefficient of the cyanobacterial gas vesicle wall. Microbiology 138, 837-845.
Walsby, A.E. (1994). Gas vesicles. Microbiol Rev 58, 94-144.
Zolochevska, O., Xia, X., Williams, B.J., Ramsay, A., Li, S., and Figueiredo, M.L. (2011). Sonoporation Delivery of Interleukin-27 Gene Therapy Efficiently Reduces Prostate Tumor Cell Growth In Vivo. Hum Gene Ther 22, 1537-1550.

* cited by examiner

ULTRASMALL GAS-FILLED PROTEIN NANOSTRUCTURES

REFERENCE TO RELATED APPLICATIONS

The present application claims the priority benefit of U.S. provisional application No. 63/336,860, filed Apr. 29, 2022, the entire contents of which are incorporated herein by reference.

STATEMENT OF FEDERALLY SPONSORED RESEARCH

This invention was made with government support under Grant Nos. R21EB033607 and R00EB024600 awarded by the National Institutes of Health. The government has certain rights in the invention.

SEQUENCE LISTING

This application contains a Sequence Listing XML, which has been submitted electronically and is hereby incorporated by reference in its entirety. Said XML Sequence Listing, created on May 1, 2023, is named RICEP0110US.xml and is XXX bytes in size.

BACKGROUND

1. Field

This disclosure relates to the fields of biology, biochemistry, molecular biology, biotechnology, and medicine. In particular, genetically engineered gas vesicle compositions with small hydrodynamic radii are provided, as well as gene clusters and methods of use thereof.

2. Related Art

Ultrasound has been one of the most used imaging and diagnostic tools in biomedicine, and its usage can be extended well beyond the conventional role of tissue imaging. For example, ultrasound-mediated gene delivery is a unique in vivo gene therapy method (Bez et al., 2019). Compared to the in vivo gene therapy using viral vectors, ultrasound-mediated gene delivery is particularly attractive because (i) it removes the concern of immune responses to viral proteins and the possible cell transformation and vector genome mobilization; (ii) ultrasound can noninvasively reach most of the human tissues, providing a unique benefit over other non-viral, physical delivery methods such as electroporation that is either limited to targets near the skin or require surgical procedures, (iii) ultrasound can be spatially focused, enabling the control the location and dose of the delivery, and (iv) ultrasound device is portable and broadly available in the clinics. Over the last decade, ultrasound-mediated gene delivery has been developed for a range of therapeutic targets such as T cells, mesenchymal stem cells (MSCs), prostate cancer cells, pancreatic islets, cardiac cells, and cells in the central nerve system (Bez et al., 2017; Chen et al., 2006; Fujii et al., 2011; Ilovitsh et al., 2020; Shimamura et al., 2004; Takeuchi et al., 2008; Zolochevska et al., 2011). Similar to gene delivery, ultrasound technologies can overcome the limitations of many conventional drug delivery methods, since ultrasound can enhance the permeability of biological barriers, increase cellular uptake of drugs, and improve the therapeutic efficacy of the delivery (Ferrara et al., 2007; Mitragotri, 2005). Further, ultrasound imaging can be used for tracking the distribution and localization of therapeutic agents within tissues (Janib et al., 2010). Such a theranostic paradigm of combining the targeting of disease biomarkers, imaging of the nano-agents, and precise delivery of drugs is critical for evaluating the success of gene and drug delivery, optimizing treatment regimens, and improving therapeutic outcomes. Overall, the use of ultrasound for imaging biomarkers and gene and drug delivery represents a promising avenue for advancing the field of disease diagnostics and personalized therapeutics.

However, many of the ultrasound technologies require the presence of microbubbles, and to this end, the size of microbubbles places a limitation on ultrasound technologies. Microbubbles are heterogeneous in size and typically cover the range of 1-5 μm in diameter (FIG. 1A), which places them on the same size scale as red blood cells and limits their biodistribution to be within the blood vessels (Lindner, 2004; Sirsi and Borden, 2009). As a result, technologies such as ultrasound-mediated gene therapy are largely limited to well-vascularized regions of a given organ and can only exert an effect on cells near the blood vessels. Synthesizing nanoparticles of the right diameter could play a critical role in optimizing the delivery efficiency in tissue (Gaumet et al., 2008); for example, for delivery to the lymph node, only molecules of 10-100 nm in hydrodynamic radius can efficiently convect into the lymphatics (Schudel et al., 2019; Swartz, 2001). Therefore, there is a critical unmet need to develop gas-filled agents with <100 nm hydrodynamic radius. Notably, nanparticles with a hydrodynamic radius below 100 nm will place the gas-filled agents at the size range of common viruses such as SARS-CoV-2 which is ~100 nm (Bar-On et al., 2020).

This invention was funded in part by the Robert A. Welch Foundation under Welch Grant No. C-2069-20210327.

SUMMARY

As provided herein, the present disclosure relates to methods of purifying proteins using genetically engineered gas vesicles or isolating cells using formulated nano- and micro-structures containing gas vesicles.

In one aspect, the present disclosure provides gas vesicle compositions comprising:

(A) a modified shell protein, wherein the amino acid sequence of the modified shell protein comprises a first fragment and a second fragment, wherein:
  - (i) the first fragment is 20-88 amino acids in length and has at least 95% sequence identity with a first wild-type gas vesicle shell protein;
  - (ii) the second fragment is 20-88 amino acids in length and has at least 95% sequence identity with a second wild-type gas vesicle shell protein;
  - and wherein the first wild-type gas vesicle shell protein and the second wild-type gas vesicle shell protein are not the same;

(B) at least one gas vesicle assembly protein independently selected from among *Bacillus megaterium* gvpR, *Bacillus megaterium* gvpN, *Bacillus megaterium* gvpF, *Bacillus megaterium* gvpG, *Bacillus megaterium* gvpL, *Bacillus megaterium* gvpS, *Bacillus megaterium* gvpK, *Bacillus megaterium* gvpJ, *Bacillus megaterium* gvpT, *Bacillus megaterium* gvpU, *Anabaena flos-aquae* gvpN, *Anabaena flos-aquae* gvpJ, *Anabaena flos-aquae* gvpK, *Anabaena flos-aquae* gvpF, *Anabaena flos-aquae* gvpG, *Anabaena flos-aquae* gvpV, and *Anabaena flos-aquae* gvpW.

In some embodiments, the at least one gas vesicle assembly protein is selected from among *Bacillus megaterium* gvpR, *Bacillus megaterium* gvpN, *Bacillus megaterium* gvpF, *Bacillus megaterium* gvpG, *Bacillus megaterium* gvpL, *Bacillus megaterium* gvpS, *Bacillus megaterium* gvpK, *Bacillus megaterium* gvpJ, *Bacillus megaterium* gvpT, and *Bacillus megaterium* gvpU. In other embodiments, the at least one gas vesicle assembly protein is selected from among *Anabaena flos-aquae* gvpN, *Anabaena flos-aquae* gvpJ, *Anabaena flos-aquae* gvpK, *Anabaena flos-aquae* gvpF, *Anabaena flos-aquae* gvpG, *Anabaena flos-aquae* gvpV, and *Anabaena flos-aquae* gvpW.

In some embodiments, the gas vesicle compositions further comprise at least one additional shell protein. In some embodiments, the modified shell protein of the gas vesicle compositions disclosed herein consists of one amino acid sequence.

In some embodiments, the first wild-type gas vesicle shell protein or the second wild-type gas vesicle shell protein is selected from among: *Anabaena flos-aquae* gvpA, *Anabaena flos-aquae* gvpC, and *Bacillus megaterium* gvpB. In further embodiments, the first wild-type gas vesicle shell protein or the second wild-type gas vesicle shell protein is *Anabaena flos-aquae* gvpA. In still further embodiments, the first fragment or the second fragment has at least 95% sequence identity with (SEQ ID NO: 1) (M1-V51 of *Anabaena flos-aquae* gvpA). In other embodiments, the first wild-type gas vesicle shell protein or the second wild-type gas vesicle shell protein is *Anabaena flos-aquae* gvpC. In still other embodiments, the first wild-type gas vesicle shell protein or the second wild-type gas vesicle shell protein is *Bacillus megaterium* gvpB. In further embodiments, the first fragment or the second fragment has 95% sequence identity with (SEQ ID NO: 2) (D52-I88 of gvpB native to *Bacillus megaterium*). In some embodiments, the first wild-type gas vesicle shell protein is *Anabaena flos-aquae* gvpA and the second wild-type gas vesicle shell protein is *Bacillus megaterium* gvpB. In further embodiments, the first fragment has 95% sequence identity with (SEQ ID NO: 1) (M1-V51 of *Anabaena flos-aquae* gvpA) and the second fragment has 95% sequence identity with (SEQ ID NO: 2) (D52-I88 of *Bacillus megaterium* gvpB). In some embodiments, the first fragment has at least 95% sequence identity with (SEQ ID NO: 1) (M1-V51 of *Anabaena flos-aquae* gvpA), the second fragment has at least 95% sequence homology with (SEQ ID NO: 2) (D52-188 of *Bacillus megaterium* gvpB), and the at least one gas vesicle assembly protein is selected from among *Bacillus megaterium* gvpR, *Bacillus megaterium* gvpN, *Bacillus megaterium* gvpF, *Bacillus megaterium* gvpG, *Bacillus megaterium* gvpL, *Bacillus megaterium* gvpS, *Bacillus megaterium* gvpK, *Bacillus megaterium* gvpJ, *Bacillus megaterium* gvpT, and *Bacillus megaterium* gvpU.

In some embodiments, the composition further comprises a therapeutic molecule.

In another aspect, the present disclosure provides polynucleotide sequences encoding a modified shell protein as described herein. In some embodiments, the polynucleotide sequence also encodes one or more gas vesicle assembly proteins selected from among *Bacillus megaterium* gvpR, *Bacillus megaterium* gvpN, *Bacillus megaterium* gvpF, *Bacillus megaterium* gvpG, *Bacillus megaterium* gvpL, *Bacillus megaterium* gvpS, *Bacillus megaterium* gvpK, *Bacillus megaterium* gvpJ, *Bacillus megaterium* gvpT, and *Bacillus megaterium* gvpU.

In another aspect, the present disclosure provides methods of treating a disease or disorder comprising administering a gas vesicle composition disclosed herein to a patient in need thereof. In some embodiments, the disease or disorder is associated with the lymphatic system. In other embodiments, the disease or disorder is associated with neuronal cells.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

FIG. 1A: Schematic of the size difference of a mammalian cell, microbubbles, wild type gas vesicles ($_{WT}$GVs), and sub-50 nm gas vesicles ($_{S50}$GVs). FIG. 1B: Protein sequence alignment of wildtype Ana GVs ($_{WT}$Ana), Mega GVs ($_{WT}$Mega), and $_{S50}$GVs. FIG. 1C: TEM images of $_{WT}$Ana, $_{WT}$Mega, $_{S50}$GVs, and commercial 50-nm gold nanoparticles ($_{50}$AuNP) (scale bar=200 nm). FIG. 1D: Mean and standard deviation (StdDev) of the particle width obtained from TEM. N=49; 112; 50 for $_{WT}$Ana, $_{WT}$Mega, $_{S50}$GVs, respectively, and the error bars represent mean±StdDev. Significance levels: ** p<0.0001. FIG. 1E: Hydrodynamic diameter comparison of $_{WT}$Ana, $_{S50}$GVs, and $_{50}$AuNP. FIG. 1**F: Zeta potential measurement conducted with N=3 biological replicates.

FIG. 2A: Schematic representation of the injection site and the targeted lymph node. FIG. 2B: IVIS images showing the transportation kinetics of injected particles. FIG. 2C: Quantitative analysis of fluorescent intensity within the targeted lymph node area. Relative intensity=lymph node area intensity/injection site intensity. FIG. 2D: Schematic representation of the histological analysis process of dissected lymph nodes, and confocal fluorescence images of immunohistochemistry to depict the distribution of $_{WT}$Ana, $_{S50}$GVs, and 50-nm gold nanoparticles ($_{50}$AuNP) within the lymph node tissues. The white dashed lines in the top row images outline the periphery of lymph nodes on the slides, and the white dashed boxes in the second row indicate the zoomed-in areas, which are shown in the bottom row. Scale bar: 500 μm in the second row and 50 μm in the third row. The images are an overlay of three images acquired in the red fluorescence channel that showed the expression of CD45, the green fluorescence channel that showed the location of the nanoparticles, and the blue fluorescence channel that showed the expression of Lyve-1.

FIG. 3A: Schematic representation of the lymphatic tissue barrier and three different methods of particle transportation: (1) particles can be transmitted into the lymph node through the endothelial cells; (2) cell-mediated transportation can carry particles into the lymph node; and (3) small particles can pass through gaps between the endothelial cells directly. FIG. 3B: Anatomical schematic of a lymph node with two windows that indicate different depths into the tissue. This figure was created with BioRender.com. The dashed black boxes illustrate areas where tissue was collected, and the black arrows indicate the relevant TEM image (FIG. 3C, FIG. 3D, or FIG. 3E) of tissue collected from each area. FIGS. 3C & 3F-H: Representative thin-section TEM images of WTAna GVs, illustrating the structure and localization of WTAna GVs within the lymph node tissue. FIGS. 3D-E & 3I-K: Representative thin-section TEM images of $_{S50}$GVs, showing the localization of $_{S50}$GVs within the lymph node tissue. For FIGS. 3C-3K, a red arrow with a white dashed line indicates GVs within the tissue. The images on the right side of FIGS. 3C-E are zoomed in views of the relevant areas labeled in each image with white windows. SCS is subcapsular sinus, L is lymphocytes, MAC is macrophages, and Ph is phagolysosomes. LV is lymph vessel.

FIG. 4A: Schematic diagram illustrating the collapse process of GVs. Light green line indicates the acoustic pressure, and the dark green line indicates the ultrasound signal from GVs. FIG. 4B: Schematic diagram demonstrating the process of generating a final 'BURST' image by subtracting B-mode images taken from the earlier frames by those from the later frames. FIG. 4C: Representative ultrasound images of the B-mode images (1st, 3rd, and 30th frame) during the high-pressure collapse process and the final 'BURST' image. The term "$_{Ctrl}$PS" refers to polystyrene beads used as a background control. FIG. 4D: Quantitative real-time intensity track for GVs and polystyrene beads ($_{Ctrl}$PS), with N=4 representative regions of interest (ROIs). FIG. 4E: Ultrasound phantom image showed the seriously diluted samples of WTAna and $_{S50}$GVs with protein concentrations of 456 μg/mL, 228 μg/mL, 114 μg/mL, and 57 μg/mL, respectively. FIG. 4F: Quantification of the signal intensity from images in FIG. 4E and other replicates. Error bars representing mean±STDEV for N=3 replicates.

DESCRIPTION OF ILLUSTRATIVE EMBODIMENTS

Figures 1A, 1B, 1C, 1D, 1E, 1F:
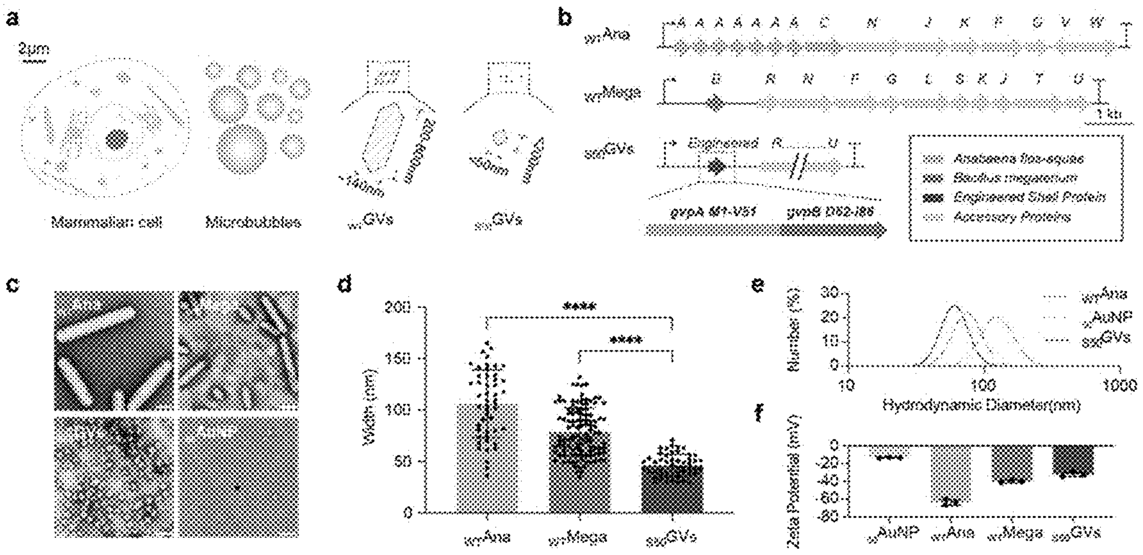
FIGS. 1A-1F illustrate the manufacturing and characterization of sub-50 nm gas-filled protein nanostructures.

The present disclosure provides sub-50 nm, stable, free-floating gas-filled protein nanostructures. The presently disclosed protein nanostructures show that genetic mutations of the major shell proteins can alter GVs into diamond-shaped nanostructures of smaller diameters. A homogenous population of these sub-50 nm GVs, which are referenced herein as $_{S50}$GVs, are favorable in that they can be produced in bacteria, purified through simple centrifugation, and remain free-floating and stable for months. Evaluation of the presently disclosed protein nanostructions demonstrates their beneficial ability to extravasate from lymph drainage into lymphatic tissues, which would gain access to the immune cells and cancer cells important nowadays for the development of tumor vaccines, early diagnostics of tumor metastasis, and the treatment of infectious diseases (Irvine and Dane, 2020; Schudel et al., 2019). The presently disclosed $_{S50}$GVs form bubbles with a beneficial combination of small hydrodynamic radius and free-floating capability. To this end, protein nanostructures of the present disclosure may be useful in a range of applications, including but not limited to enabling ultrasound technologies to cells previously inaccessible by microbubbles and nanobubbles. Additional details on these aspects and more are provided above and in the sections that follow.

I. GAS VESICLES

Gas vesicles (GVs) are a class of gas-filled hollow protein nanostructures found inside photosynthetic microorganisms, which use them to float in bodies of water to compete for maximal photosynthesis (Pfeifer, 2012). The wildtype GVs are usually found to be cylindrical or spindle shape with a diameter ranging between 70 to 300 nm, and in the case of cylindrical GVs, the length is believed to be unregulated and usually much longer than the diameter (Walsby, 1994). Although named "vesicles", GVs are made of only proteins, which form 3-nm shells. Notably, GVs have a fundamentally different design principle compared to synthetic bubbles. The design of bubbles usually aims to minimize the leaking of interior gas to the outside; however, as the leaking still occurs, the bubbles will eventually shrink and disappear. Such leaking becomes more pronounced as one reduces the diameter of the bubbles, since the smaller bubbles give rise to higher surface tensions and a higher pressure buildup of the interior gas (Brennen, 1995). This is the fundamental reason that it has been challenging to reduce the diameter of synthetic bubbles, which only reached ~200 nm recently with a strengthened shell (Jafari Sojahrood et al., 2021). For GVs, however, nature evolved them to be permeable to both gas and water molecules. The way for GVs to keep liquid water from forming inside is to have a highly hydrophobic inner surface that prevents water molecular from undergoing heterogeneous condensation into liquid droplets, and to have the sub-micron size of the air compartment that substantially reduces the chance of homogeneous condensation, i.e., the spontaneous formation of droplets in a cavity. The 3 nm-thin protein shell of GVs can withstand multiple atmospheric pressure, thus withstanding the surface tension required to form ultrasmall nanobubbles. It has been established that the sequence of the major shell protein of GVs is the primary determinant of the diameter of GVs (Walsby et al., 1992). The present disclosure describes mutations to amino acid sequences of shell proteins that result in a reduction of the GV diameter and formation of ultrasmall nanobubbles.

The gas vesicle compositions described herein have a useful and notably small free-floating bubbles. In comparison, gas encapsulated in synthetic microbubbles and nanobubbles or vaporized from nanodroplets tends to leak to the surrounding liquid, which makes such gas-filled nanoagents fundamentally unstable. In some embodiments, the diameter of the presently disclosed gas vesicle compositions is less than about 100 nm. In some embodiments, the diameter of the presently disclosed gas vesicle compositions is about 30 nm, about 31 nm, about 32 nm, about 33 nm, about 34 nm, about 35 nm, about 36 nm, about 37 nm, about 38 nm, about 39 nm, about 40 nm, about 41 nm, about 42 nm, about 43 nm, about 44 nm, about 45 nm, about 46 nm, about 47 nm, about 48 nm, about 49 nm, about 50 nm, about 51 nm, about 52 nm, about 53 nm, about 54 nm, about 55 nm, about 56 nm, about 57 nm, about 58 nm, about 59 nm, about 60 nm, or any range derivable therein. In some embodiments, the diameter of the presently disclosed gas vesicle compositions is between about 40 nm and about 60 nm. In some embodiments, the diameter of the presently disclosed gas vesicle compositions is less than about 50 nm. In some embodiments, the diameter is between about 40 nm and about 50 nm. In some embodiments, the diameter of the presently disclosed gas vesicle compositions is about 46 nm. Bubbles on the scale of 1 nm have been described, but they require the presence of a graphene interface and are thus not free-floating (Khestanova et al., 2016).

In some embodiments, the presently disclosed gas vesicle compositions may be useful in the delivery of therapies to the lymphatic system, particularly lymphocytes. Lymph nodes have been associated with various immunology studies and developments of therapeutic interventions. The presently disclosed gas vesicle compositions may, without being bound by theory, facilitate the use of new technologies in these studies. As described in further detail below, gas vesicle compositions of the present disclosure accumulate within the subcapsular area and lymph vessels, and a sizable quantity of the presently disclosed gas vesicle compositions cross the tissue barrier to gain access to lymphocytes. Moreover, a significant fraction of presently disclosed gas vesicle was detected within the deeper tissue, either with the lymphocytes or within the phagosome of some antigen-presenting cells. Overall, the present invention enables a minimally invasive and clinically translatable method for ultrasound-mediated delivery to lymphatic cells that were previously inaccessible to these ultrasound technologies.

The ultrasmall size of the presently disclosed gas vesicle compositions will enable them to cross various biological barriers in addition to the lymphatic endothelial cell layer demonstrated in this work. This might include, without being bound by theory, the blood-brain barrier (BBB), which has been a focal point of recent research for developing treatment of neurological diseases (Banks, 2016). Considerable information has been collected that indicates nanoparticles between 50-200 nm would be ideal to cross the BBB (Arvanitis et al., 2020; Terstappen et al., 2021). The presently disclosed gas vesicle compositions may be useful in such applications, especially considering that the surface coating such as polyethylene glycol may be needed to elongate the blood circulation time and would slightly increase the size of the gas vesicle compositions disclosed herein. Ultrasound-driven, microbubble-based BBB opening has been established as a method to enhance the transport of viral vectors and nanoparticles into the brain tissues. The presently disclosed gas vesicle compositions may therefore be useful in combination with synthetic microbubbles, where the stable cavitation of synthetic microbubbles will drive BBB opening to enhance the entry of gas vesicle compositions disclosed herein into the brain, followed by the use of presently disclosed gas vesicle compositions to image biomarkers or carry cargos to the surface of neuronal cells for delivery. Lastly, the ultrasound signal from presently disclosed gas vesicle compositions can be used to track their distribution within the tissue, which provides key information for monitoring the process of gene and drug delivery, and to this end, presently disclosed gas vesicle compositions represent a dual nano-agents that can be simultaneously used for delivery and tracking.

Furthermore, as discussed in more detail below, gas vesicle compositions disclosed herein generate ultrasound signals. Optimization of presently disclosed gas vesicle compositions may result in useful biosensors to reversibly detect cellular processes. Implementation of the fast plane-wave imaging during the collapse process of GVs, as demonstrated in the BURST method (Sawyer et al., 2021), may, for example, produce a stronger signal than the B-mode imaging described in the Examples section below. To this end, since presently disclosed gas vesicle compositions have higher critical collapse pressure than wildtype gas vesicles, it is possible, without being bound by theory, that either a lower frequency ultrasound transducer, such as the 10 and 11 MHz transducers used in the BURST method, or a transducer designed with enhanced pressure output may to enhance the vesicles. Secondly, the ultrasound contrast of the presently disclosed gas vesicle compositions can be enhanced through molecular engineering of their clustering state, because, without being bound by theory, clustering will nonlinearly increase the scattering cross section and thus substantially increase the ultrasound contrast as demonstrated in the case of wildtype GVs (Shapiro et al., 2014). For example, the presently disclosed gas vesicle compositions may comprise proteins that induce clustering (Li et al., 2023), or clustering may be induced during phagocytosis or cell binding to obtain biosensors comprising the presently disclosed gas vesicle compositions that are useful for reversibly detecting cellular processes.

Wildtype Gas Vesicle Shell Proteins

Shell proteins are important structural proteins required for the formation of wildtype gas vesicles. The composition of gas vesicles with respect to both the number of copies of shell proteins, the number of different shell proteins, and the identity of required shell proteins, varies by microorganism. For example, the shell protein of wildtype cyanobacterium *Anabaenae flos-aquae* comprises two primary shell proteins: gvpA and gvpC (see WTAna of FIG. 1B). A natively produced gas vesicle of *A. flos-aquae* has seven copies of gvpA and one copy of gvpC. GvpA is the major gas vesicle structural protein of *A. flos-aquae* and, consistent with comments above, is amphiphilic. Aggregation of gvpA, which has a coil-α-β-β-α-coil structure, leads to the formation of the helical ribs of the gas vesicle. GvpC is a second structural protein which binds to the exterior of the gas vesicle and provides reinforcement and affects the formation of the cylindrical shape of the wildtype *A. flos-aquae* gas vesicle. In *Bacillus megaterium*, the primary shell protein is gvpB, which has a high homology to known gvpA shell proteins. Details of shell proteins of various microorganisms are described, for example, in Pfeifer, 2022, van Keulen et al, 2005, and Pfeifer 2006, all of which are incorporated herein by reference. Sequences of wildtype shell proteins are known in the art and can be found, for example, on public databases such as https://www.uniprot.org/, which is incorporated herein in its entirety by reference.

Wildtype Gas Vesicle Accessory Proteins

Wildtype gas vesicles comprise further accessory proteins which, as with the shell proteins described above, vary in number of copies of accessory proteins, the number of different accessory proteins, and the identity of accessory proteins based on the microorganism where they are natively produced. These proteins may have a variety of functions, including but not limited to serving as chaperones, delivering energy, regulating transcription, or facilitating protein complex formation. Some accessory proteins are not required for formation of gas vesicles. Accessory proteins may also have useful hydrophilic or hydrophobic characteristics. Details of accessory proteins of various microorganisms are described, for example, in Pfeifer, 2022, van Keulen et al, 2005, and Pfeifer 2006, all of which are incorporated herein by reference. Sequences of wildtype accessory proteins are known in the art and can be found, for example, on public databases such as https://www.uniprot.org/, which is incorporated herein in its entirety by reference.

Modified Shell Proteins

The present disclosure provides gas vesicles wherein the shell protein is a modified shell protein. The modified shell protein of presently disclosed gas vesicles comprises at least two amino acid residue fragments that each have substantial sequence identity with the amino acid sequence of different wildtype gas vesicle shell proteins, as described above.

The first amino acid residue fragment may in some embodiments be about 10 amino acids, about 12 amino acids, about 14 amino acids, about 16 amino acids, about 18 amino acids, about 20 amino acids, about 22 amino acids, about 24 amino acids, about 26 amino acids, about 28 amino acids, about 30 amino acids, about 32 amino acids, about 34 amino acids, about 36 amino acids, about 38 amino acids, about 40 amino acids, about 42 amino acids, about 44 amino acids, about 46 amino acids, about 48 amino acids, about 50 amino acids, about 52 amino acids, about 54 amino acids, about 56 amino acids, about 58 amino acids, about 60 amino acids, about 62 amino acids, about 64 amino acids, about 66 amino acids, about 68 amino acids, about 70 amino acids, about 72 amino acids, about 74 amino acids, about 76 amino acids, about 78 amino acids, about 80 amino acids, about 82 amino acids, about 84 amino acids, about 86 amino acids, about 88 amino acids, about 90 amino acids, about 92 amino acids, about 94 amino acids, about 96 amino acids, about 98 amino acids, or about 100 amino acids in length, or any range derivable therein. In some embodiments, the first amino acid fragment of the modified shell protein is between about 20 to about 88 amino acids in length. In some embodiments, the first fragment is between about 40 and about 60 amino acid residues in length. In some embodiments, the first fragment is about 50 amino acid residues in length. In some embodiments, the first fragment is between about 20 and about 40 amino acid residues in length. In some embodiments, the first fragment is between about 30 and about 40 amino acid residues in length. In some embodiments, the first fragment is about 36 amino acid residues in length.

As mentioned above, the first fragment has substantial sequence identity with the amino acid sequence of a wild-type shell protein. In some embodiments, the first fragment has at least about 90%, about 91%, about 92%, about 93%, about 94%, about 95%, about 96%, about 97%, about 98%, or about 99% sequence identity with a wildtype shell protein, or any range derivable therein. In some embodiments, the first fragment has at least about 95% sequence identity with a wildtype gas vesicle shell protein. In some embodiments, the first fragment has at least about 98% sequence identity with a wildtype gas vesicle shell protein.

The first amino acid residue fragment may have substantial sequence identity with any portion of a wildtype shell protein. For example, in some embodiments the first amino acid fragment may have substantial sequence identity with the C-terminus of a wildtype shell protein. In some embodiments the first amino acid fragment may have substantial sequence identity with the N-terminus of a wildtype shell protein. In some embodiments the first amino acid fragment may have substantial sequence identity with a portion of the amino acid sequence of a wildtype shell protein that is between the N-terminus and the C-terminus of the wildtype shell protein.

The first fragment may have substantial sequence identity with a gas vesicle shell protein from any microorganism that natively produces gas vesicles. In some embodiments, the first fragment has substantial sequence identity with a gas vesicle shell protein that is natively produced by bacteria, such as cyanobacteria or soil bacteria, or a haloarchaea. In some embodiments, the first fragment has substantial sequence identity with a gas vesicle shell protein natively formed in a cyanobacteria. In some embodiments, the first fragment has substantial sequence identity with a gas vesicle shell protein natively formed in *Anabaena flos-aquae*. In some embodiments, the first fragment has substantial sequence identity with *Anabaena flos-aquae* gvpA. In some embodiments, the first fragment has substantial sequence identity with *Anabaena flos-aquae* gvpC.

In some embodiments, the first fragment has substantial sequence identity with a gas vesicle shell protein natively formed in soil bacteria. In some embodiments, the first fragment has substantial sequence identity with a gas vesicle shell protein natively formed in *Bacillus megaterium*. In some embodiments, the first fragment has substantial sequence identity with *Bacillus megaterium*. gvpB.

The second amino acid residue fragment may in some embodiments be about 10 amino acids, about 12 amino acids, about 14 amino acids, about 16 amino acids, about 18 amino acids, about 20 amino acids, about 22 amino acids, about 24 amino acids, about 26 amino acids, about 28 amino acids, about 30 amino acids, about 32 amino acids, about 34 amino acids, about 36 amino acids, about 38 amino acids, about 40 amino acids, about 42 amino acids, about 44 amino acids, about 46 amino acids, about 48 amino acids, about 50 amino acids, about 52 amino acids, about 54 amino acids, about 56 amino acids, about 58 amino acids, about 60 amino acids, about 62 amino acids, about 64 amino acids, about 66 amino acids, about 68 amino acids, about 70 amino acids, about 72 amino acids, about 74 amino acids, about 76 amino acids, about 78 amino acids, about 80 amino acids, about 82 amino acids, about 84 amino acids, about 86 amino acids, about 88 amino acids, about 90 amino acids, about 92 amino acids, about 94 amino acids, about 96 amino acids, about 98 amino acids, or about 100 amino acids in length, or any range derivable therein. In some embodiments, the second amino acid fragment of the modified shell protein is between about 20 to about 88 amino acids in length. In some embodiments, the second fragment is between about 40 and about 60 amino acid residues in length. In some embodiments, the second fragment is about 50 amino acid residues in length. In some embodiments, the second fragment is between about 20 and about 40 amino acid residues in length. In some embodiments, the second fragment is between about 30 and about 40 amino acid residues in length. In some embodiments, the second fragment is about 36 amino acid residues in length.

As mentioned above, the second fragment has substantial sequence identity with the amino acid sequence of a wild-type shell protein. In some embodiments, the second fragment has at least about 90%, about 91%, about 92%, about 93%, about 94%, about 95%, about 96%, about 97%, about 98%, or about 99% sequence identity with a wildtype shell protein, or any range derivable therein. In some embodiments, the second fragment has at least about 95% sequence identity with a wildtype gas vesicle shell protein. In some embodiments, the second fragment has at least about 98% sequence identity with a wildtype gas vesicle shell protein.

The second amino acid residue fragment may have substantial sequence identity with any portion of a wildtype shell protein. For example, in some embodiments the second amino acid fragment may have substantial sequence identity with the C-terminus of a wildtype shell protein. In some embodiments the second amino acid fragment may have substantial sequence identity with the N-terminus of a wildtype shell protein. In some embodiments the second amino acid fragment may have substantial sequence identity with a portion of the amino acid sequence of a wildtype shell protein that is between the N-terminus and the C-terminus of the wildtype shell protein.

The second fragment may have substantial sequence identity with a gas vesicle shell protein from any microorganism that natively produces gas vesicles. In some embodiments, the second fragment has substantial sequence identity with a gas vesicle shell protein that is natively produced by bacteria, such as cyanobacteria or soil bacteria, or by haloarchaea. In some embodiments, the second fragment has substantial sequence identity with a gas vesicle shell protein natively formed in cyanobacteria. In some embodiments, the second fragment has substantial sequence identity with a gas vesicle shell protein natively formed in *Anabaena flos-aquae*. In some embodiments, the second fragment has substantial sequence identity with *Anabaena flos-aquae* gvpA. In some embodiments, the second fragment has substantial sequence identity with *Anabaena flos-aquae* gvpC.

In some embodiments, the second fragment has substantial sequence identity with a gas vesicle shell protein natively formed in soil bacteria. In some embodiments, the second fragment has substantial sequence identity with a gas vesicle shell protein natively formed in *Bacillus megaterium*. In some embodiments, the second fragment has substantial sequence identity with *Bacillus megaterium* gvpB.

The modified shell proteins of the presently disclosed gas vesicle compositions comprise fragments with substantial sequence identity to at least two different wildtype gas vesicle shell proteins. The two different wildtype gas vesicle shell proteins of modified shell proteins of the present disclosure may be any gas vesicle shell protein produced by any microorganism. The modified shell proteins in some embodiments comprise a fragment with substantial sequence identity to a gas vesicle shell protein natively produced by *Anabaena flos-aquae* and a fragment with substantial sequence identity to a gas vesicle shell protein natively produced by *Bacillus megaterium*. The modified shell proteins in some embodiments comprise a fragment with substantial sequence identity with *Anabaena flos-aquae* gvpA and a fragment with substantial sequence identity to *Bacillus megaterium* gvpB. The modified shell proteins in some embodiments comprise a fragment with substantial sequence identity with *Anabaena flos-aquae* gvpA and a fragment with substantial sequence identity with *Anabaena flos-aquae* gvpC. In some embodiments, the modified shell proteins in some embodiments comprise a fragment with substantial sequence identity with *Anabaena flos-aquae* gvpC and a fragment with substantial sequence identity to *Bacillus megaterium* gvpB. The presently disclosed modified shell proteins may in some embodiments comprise more than two fragments, such as three fragments or four fragments, each with substantial sequence identity to independently selected amino acid sequences of two or more different wildtype gas vesicle shell proteins.

In some embodiments, the gas vesicle composition comprises about one, about two, about three, about four, about five, about six, about seven, about eight, about nine, or about ten copies of a modified shell protein as described above. The gas vesicle compositions disclosed herein may comprise multiple types of modified shell proteins, wherein in a type of modified shell protein is defined herein as possessing one combination of a first fragment and a second fragment. The gas vesicles of the present disclosure, therefore, may in some embodiments comprise a modified shell protein with an amino acid sequence according to the details provided above, and a second modified shell protein with a different amino acid sequence. In some embodiments, all present copies of the modified shell protein have approximately the same amino acid sequence.

The gas vesicles of the present disclosure may further comprise wildtype gas vesicle shell proteins, such as *Anabaena flos-aquae* gvpA, *Anabaena flos-aquae* gvpC, *Bacillus megaterium* gvpB, or any other natively produced gas vesicle shell protein known in the art. The gas vesicles of the present disclosure may in some embodiments comprise about one, about two, about three, about four, about five, about six, about seven, about eight, about nine, or about ten copies of a wildtype gas vesicle shell protein.

The presently disclosed gas vesicles comprise a modified shell protein and at least one gas vesicle assembly protein, details of which are provided above. In some embodiments, the gas vesicle assembly protein is selected from among *Bacillus megaterium* gvpR, *Bacillus megaterium* gvpN, *Bacillus megaterium* gvpF, *Bacillus megaterium* gvpG, *Bacillus megaterium* gvpL, *Bacillus megaterium* gvpS, *Bacillus megaterium* gvpK, *Bacillus megaterium* gvpJ, *Bacillus megaterium* gvpT, *Bacillus megaterium* gvpU, *Anabaena flos-aquae* gvpN, *Anabaena flos-aquae* gvpJ, *Anabaena flos-aquae* gvpK, *Anabaena flos-aquae* gvpF, *Anabaena flos-aquae* gvpG, *Anabaena flos-aquae* gvpV, and *Anabaena flos-aquae* gvpW. In some embodiments, the gas vesicle assembly protein is selected from among *Bacillus megaterium* gvpR, *Bacillus megaterium* gvpN, *Bacillus megaterium* gvpF, *Bacillus megaterium* gvpG, *Bacillus megaterium* gvpL, *Bacillus megaterium* gvpS, *Bacillus megaterium* gvpK, *Bacillus megaterium* gvpJ, *Bacillus megaterium* gvpT, and *Bacillus megaterium* gvpU. In some embodiments, the at least one gas vesicle assembly protein is selected from among *Anabaena flos-aquae* gvpN, *Anabaena flos-aquae* gvpJ, *Anabaena flos-aquae* gvpK, *Anabaena flos-aquae* gvpF, *Anabaena flos-aquae* gvpG, *Anabaena flos-aquae* gvpV, and *Anabaena flos-aquae* gvpW.

In some embodiments, the presently disclosed gas vesicle compositions comprise the assembly proteins of a wildtype gas vesicle. In some embodiments, the presently disclosed gas vesicle compositions comprise the assembly proteins of the wildtype gas vesicles of *Bacillus megaterium*. In some embodiments, the presently disclosed gas vesicle compositions comprise the assembly proteins of the wildtype gas vesicles of *Anabaena flos-aquae*. In some embodiments, the presently disclosed gas vesicle compositions comprise a combination wildtype gas vesicle.

II. PROCESS SCALE-UP

The methods for forming the gas vesicle compositions described herein can be further modified and optimized, including for preparative, pilot- or large-scale production, either batch of continuous, using the principles and techniques of process chemistry, bacterial growth, or bioprocessing as applied by a person skilled in the art. Such principles and techniques are taught, for example, in Practical Process Research & Development (2000), which is incorporated by reference herein. To enhance the production of presently disclosed gas vesicle compositions in *E. coli* hosts, the culture conditions and protein purification procedures may be altered from those disclosed in the Examples section. Optimizing the expression system could, for example, involve modifying the promoter, selecting a more suitable host strain, or utilizing alternative protein production platforms. Adjustment of the induction condition, culture temperature, or length of protein expression may, without being bound by theory, enhance the yield of the presently disclosed gas vesicle compositions. Lastly, to improve protein purity and yield, efforts can be made to optimize the purification process and unclustering procedures as described in the Examples section.

III. DEFINITIONS

The terms "polynucleotide," "nucleic acid" and "transgene" are used interchangeably herein to refer to all forms of nucleic acid, oligonucleotides, including deoxyribonucleic acid (DNA) and ribonucleic acid (RNA) and polymers thereof. Polynucleotides include genomic DNA, cDNA and antisense DNA, and spliced or unspliced mRNA, rRNA, tRNA and inhibitory DNA or RNA (RNAi, e.g., small or short hairpin (sh)RNA, microRNA (miRNA), small or short interfering (si)RNA, trans-splicing RNA, or antisense RNA). Polynucleotides can include naturally occurring, synthetic, and intentionally modified or altered polynucleotides (e.g., variant nucleic acid). Polynucleotides can be single stranded, double stranded, or triplex, linear or circular, and can be of any suitable length. In discussing polynucleotides, a sequence or structure of a particular polynucleotide may be described herein according to the convention of providing the sequence in the 5' to 3' direction.

A nucleic acid encoding a polypeptide often comprises an open reading frame that encodes the polypeptide. Unless otherwise indicated, a particular nucleic acid sequence also includes degenerate codon substitutions.

Nucleic acids can include one or more expression control or regulatory elements operably linked to the open reading frame, where the one or more regulatory elements are configured to direct the transcription and translation of the polypeptide encoded by the open reading frame in a mammalian cell. Non-limiting examples of expression control/regulatory elements include transcription initiation sequences (e.g., promoters, enhancers, a TATA box, and the like), translation initiation sequences, mRNA stability sequences, poly A sequences, secretory sequences, and the like. Expression control/regulatory elements can be obtained from the genome of any suitable organism.

A "promoter" refers to a nucleotide sequence, usually upstream (5') of a coding sequence, which directs and/or controls the expression of the coding sequence by providing the recognition for RNA polymerase and other factors required for proper transcription. "Promoter" includes a minimal promoter that is a short DNA sequence comprised of a TATA-box and optionally other sequences that serve to specify the site of transcription initiation, to which regulatory elements are added for control of expression.

An "enhancer" is a DNA sequence that can stimulate transcription activity and may be an innate element of the promoter or a heterologous element that enhances the level or tissue specificity of expression. It is capable of operating in either orientation (5'->3' or 3'->5'), and may be capable of functioning even when positioned either upstream or downstream of the promoter.

Promoters and/or enhancers may be derived in their entirety from a native gene, or be composed of different elements derived from different elements found in nature, or even be comprised of synthetic DNA segments. A promoter or enhancer may comprise DNA sequences that are involved in the binding of protein factors that modulate/control effectiveness of transcription initiation in response to stimuli, physiological or developmental conditions.

The term "substantial identity" in the context of a polypeptide indicates that a polypeptide comprises a sequence with at least 70%, 71%, 72%, 73%, 74%, 75%, 76%, 77%, 78%, or 79%, or 80%, 81%, 82%, 83%, 84%, 85%, 86%, 87%, 88%, or 89%, or at least 90%, 91%, 92%, 93%, or 94%, or even, 95%, 96%, 97%, 98% or 99%, sequence identity to the reference sequence over a specified comparison window. An indication that two polypeptide sequences are identical is that one polypeptide is immunologically reactive with antibodies raised against the second polypeptide. Thus, a polypeptide is identical to a second polypeptide, for example, where the two peptides differ only by a conservative substitution.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects or patients. Unless otherwise noted, the term "about" is used to indicate a value of ±10% of the reported value, preferably a value of ±5% of the reported value. It is to be understood that, whenever the term "about" is used, a specific reference to the exact numerical value indicated is also included."

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The terms "treat" and "treatment" refer to both therapeutic treatment and prophylactic or preventative measures, wherein the object is to prevent, inhibit, reduce, or decrease an undesired physiological change or disorder, such as the development, progression or worsening of the disorder. For purposes of this invention, beneficial or desired clinical results include, but are not limited to, alleviation of symptoms, diminishment of extent of disease, stabilizing a (i.e., not worsening or progressing) symptom or adverse effect of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those predisposed (e.g., as determined by a genetic assay).

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

IV. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

A. Modifying the Size and Shape of Gas Vesicles by Genetic Engineering

In a recent design and screening of various shell protein variants composed of hybrid protein sequences from *Anabaena flos-aquae* and *Bacillus megaterium* (Li et al., 2023), a genetic variant was uncovered that consists of MAVEKTNSSSSLAEVIDRILDK-GIVIDAWVRVSLVGIELLAIEARIVIASV (SEQ ID NO: 1), the N-terminus to the 2nd β-sheet of gvpA from *A. flos-aquae* (residues M1-V51), and DTWLRY-AEAVGLLRDDVEENGLPERSNSSEGQPRFSI (SEQ ID NO: 2), the 2nd α helix to the C-terminus of gvpB from *B. megaterium* (residues D52-I88) (FIG. 1B). After test expression of this genetic variant of GVs in *E. coli* and centrifugally assisted flotation, a visible white layer was observed, indicating the presence of GVs. Upon the TEM imaging, these GVs were discovered to display a homogenous population of diamond-shape nanostructures with a diameter less than 50 nm (FIG. 1C), thus representing a highly interesting type of ultrasmall GVs that were termed $_{S50}$GV.

B. Nanoparticle Characterization of $_{S50}$GV

Next, the dimensions, hydrodynamic diameter, surface charge, and yield of $_{S50}$GV were quantitatively characterized. First, the size of $_{S50}$GV was quantified by measuring the particles on multiple TEM images, and the wildtype *A. flos-aquae* GVs ($_{WT}$Ana), the wildtype *B. megaterium* GVs ($_{WT}$Mega), and commercially available 50-nm gold nanoparticles ($_{50}$AuNP) were included as control samples (FIG. 1C and FIG. 1D). The quantification established the diameter of $_{S50}$GV to be 46.39±10.91 nm, which demonstrated that the $_{S50}$GV has over 10 times smaller volume than the $_{WT}$Ana. Subsequently, the geometrical calculation previously described for $_{WT}$Ana and $_{WT}$Mega GVs with the approximate shell thickness and protein density (Lakshmanan et al., 2017) was followed, and the molecular weight and gas volume of $_{S50}$GV (Table 1) was obtained.

TABLE 1

Characterization of gas vesicle variants

| GV variants | $_{WT}$Ana | $_{WT}$Mega | $_{S50}$GV |
|---|---|---|---|
| Diameter, mean value (nm) | 106.12 | 78.92 | 46.39 |
| Diameter, standard deviation (nm) | 32.9 | 23.31 | 10.91 |
| Number of particles counted from TEM images | 49 | 112 | 50 |
| GV molecular weight (MDa) | 252.57 | 77.17 | 7.71 |
| GV volume (attoliter) | 4.07 | 0.85 | 0.0293 |
| Gas volume (attoliter) | 3.77 | 0.759 | 0.0202 |
| Gas volume per mg/mL of protein (v/v %/[mg/mL]) | 0.91 | 0.59 | 0.16 |

After establishing the dimensions of $_{S50}$GV in dried conditions, their behavior was characterized in hydrated conditions to predict their behavior more accurately in biomedical applications. The hydrodynamic diameters of $_{WT}$Ana, $_{S50}$GV, $_{50}$AuNP were measured, and $_{S50}$GV showed a diameter of 63.56±1.26 nm, which was smaller than 79.21±1.28 nm measured from the commercial $_{50}$AuNP (FIG. 1E). Thirdly, the surface charge measured as Zeta potential showed that $_{S50}$GVs are comparable to $_{WT}$Ana and $_{WT}$Mega GVs (FIG. 1F). Lastly, through expression and purification of $_{S50}$GV from repeated batches of *E. coli*, the yield of $_{S50}$GV was determined to be approximately 0.5 mg/L after the unclustering procedure. Notably, the yield was not fully optimized in the above experiments, and results could, without being bound by theory, be improved by optimizing any one or a combination of the induction time or temperature, the assembly process, or the unclustering procedure.

Figures 2A, 2B, 2C, 2D:
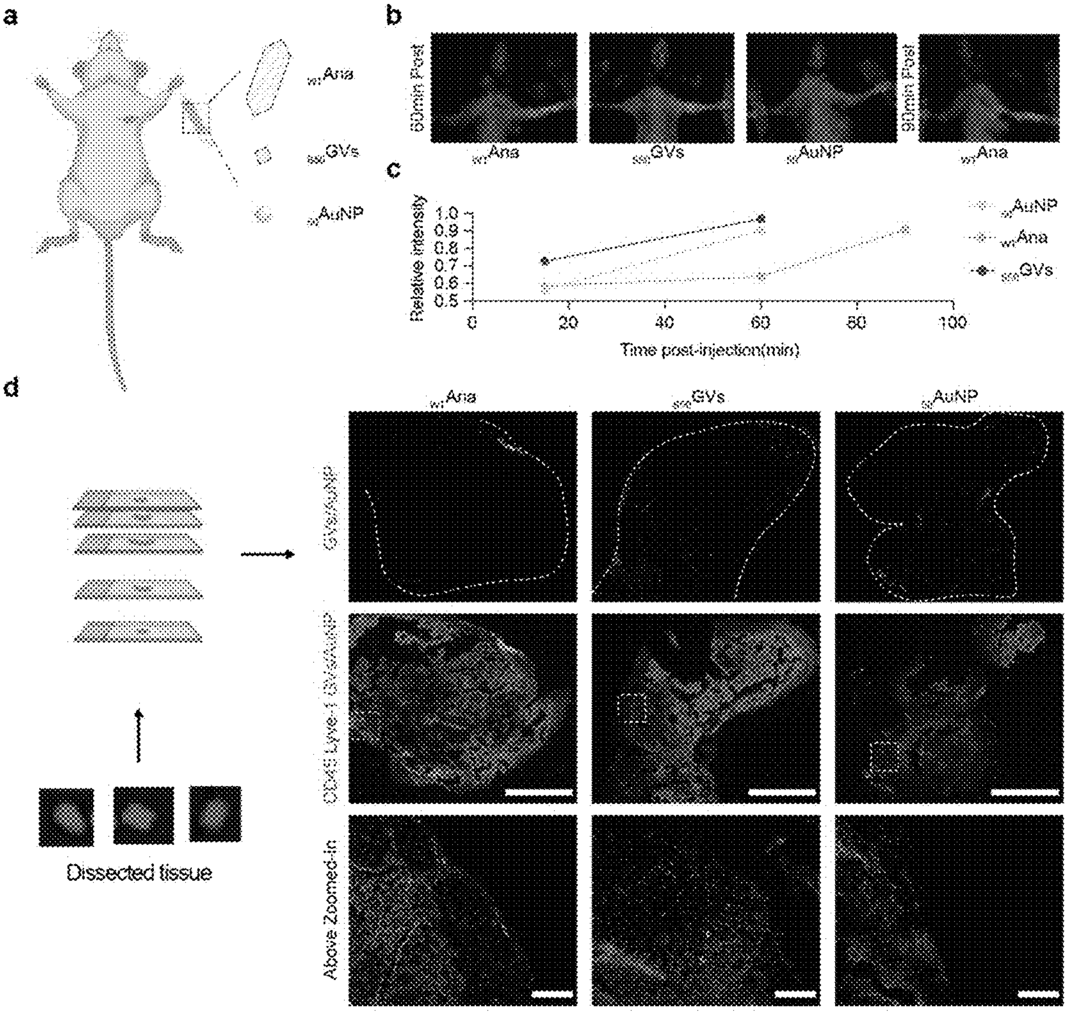
FIGS. 2A-2D show the biodistribution of nanoparticles in lymph nodes.

C. $_{S50}$GV can Penetrate the Barrier of Lymphatic Endothelial Cells and Gain Access to Immune Cells To evaluate the ability of $_{S50}$GVs to reach previously inaccessible cell populations, the biodistribution of $_{S50}$GV in lymph nodes after interstitial injection was studied. To assess the $_{S50}$GVs' accessibility to the lymphatic system, fluorescently labeled $_{S50}$GV, $_{WT}$Ana GVs, and 50-nm gold nanoparticles were prepared. First, the same amount of nanoparticles were interstitially injected into the front paw of mice and access to the nearby lymph node, which in this case was the axillary lymph node, was compared (FIG. 2A). Two key indices, the particles' perfusion speed and their location within the lymph node tissue, were monitored to determine whether the GVs were able to penetrate into the lymphatic tissue. The fluorescence live animal imaging revealed that, at about 60 minutes post-injection, a relatively high intensity of signals from the targeted lymph node for both the $_{S50}$GV and $_{50}$AuNP groups (FIG. 2B and FIG. 2C) was observed. However, for the $_{WT}$Ana group, it took about 90 minutes post-injection for the lymph node area to achieve a similar fluorescent intensity. Once all lymph node areas achieved a similar relative fluorescent intensity, the lymph node was dissected and immunohistology analysis was conducted (FIG. 2D). For $_{WT}$Ana GVs, most of them were aggregated within the surface area of the lymph node, which is the capsular or small part of the subcapsular space, and in the zoomed-in images, $_{WT}$Ana GV signals were colocalized with the lymphatic vessels, which are highly present in the capsular area. In comparison, the $_{S50}$GVs and 50-nm AuNP were able to penetrate deeper into the lymph node and spread across a wider area throughout the tissue, shown by their co-localization with leukocytes labeled with CD45 antibodies and away from the lymphatic vessels labeled with Lyve-1 dyes. These data indicate, without being bound by theory, that $_{S50}$GVs are able to extravasate out from the lymph drainage and access the leukocytes, consistent with knowledge of the cut-off size of lymphatic endothelial cells.

Figures 3A, 3B, 3C, 3D, 3E, 3F, 3G, 3H, 3I, 3J, 3K:
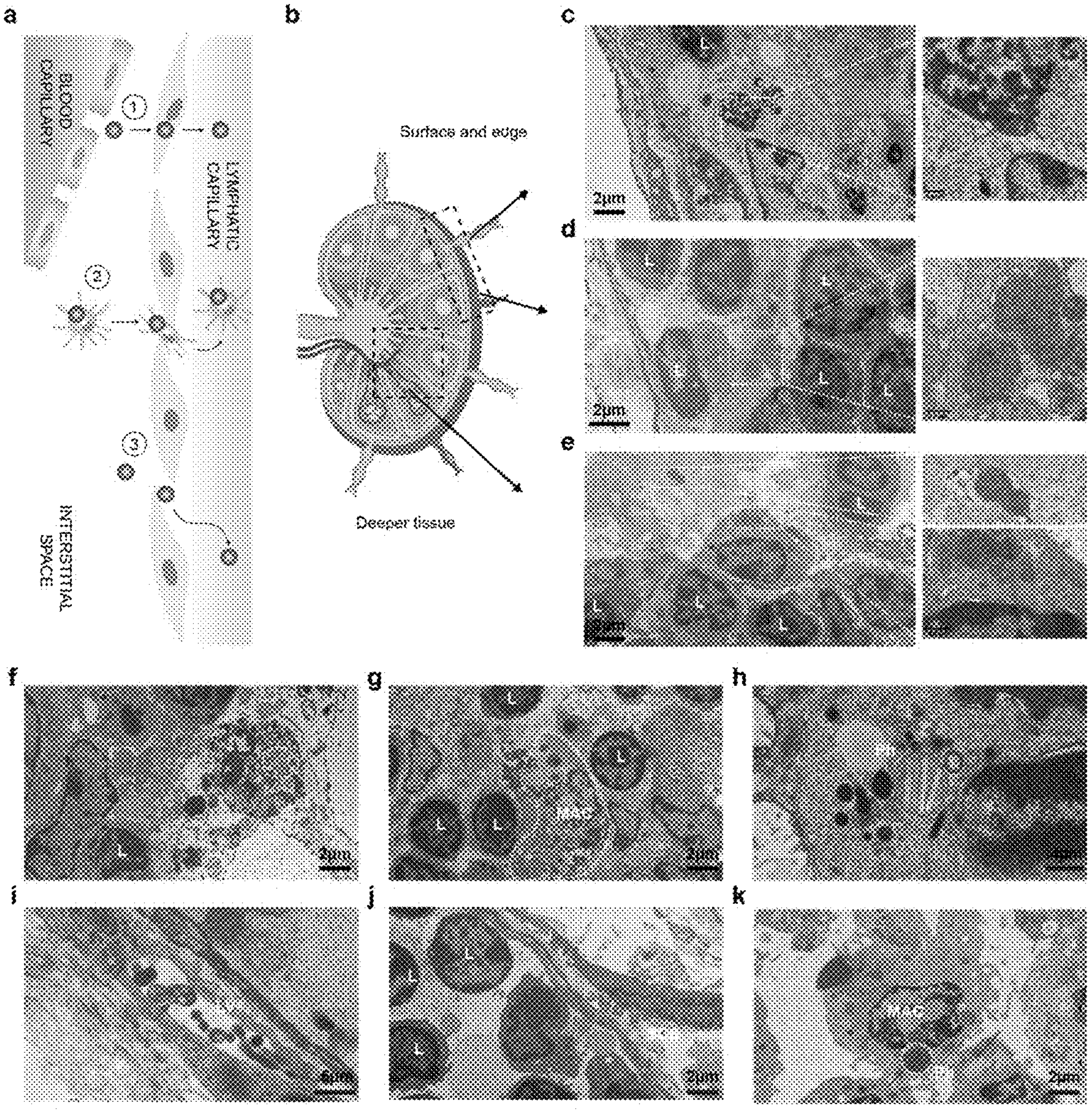
FIGS. 3A-3K show the sub-cellular localization of $_{WT}$Ana GVs and $_{S50}$GVs by thin-sectioned TEMs.

D. Thin-Sectioned TEM Images Revealed the Subcellular Distribution of $_{S50}$GV To obtain a more detailed understanding of the location of the injected nanoparticles, transmission electron microscopy of ultra-thin sectioned tissue was utilized to image harvested lymph node ultrastrucuture. Different regions of the lymph nodes were screened (FIG. 3B) and it was discovered that some shorter $_{WT}$Ana GVs can accumulate within the subcapsular sinus (FIG. 3C). Furthermore, almost no $_{WT}$Ana GVs were detected within the lymphatic tissue at the early timepoint (60 min); and at the late timepoint sample (90 min), only a small amount of $_{WT}$Ana GVs was detected that were predominantly located within antigen-presenting cells, such as macrophages (FIGS. 3D-3F). In contrast, a large number of $_{S50}$GVs accumulated within the subcapsular area (FIG. 3G) and lymph vessels (FIG. 3H). A substantial quantity of $_{S50}$GVs were found to have crossed the lymphatic endothelial cell barrier and be located deep in lymphatic tissues (FIG. 3I and FIG. 3J). Both $_{S50}$GVs and $_{WT}$Ana GVs were observed primarily within the endocytosed compartments such as phagosomes of antigen-presenting cells.

E. $_{S50}$GVs Exhibit a Distinctive Ultrasound Signal

Figures 4A, 4B, 4C, 4D, 4E, 4F:
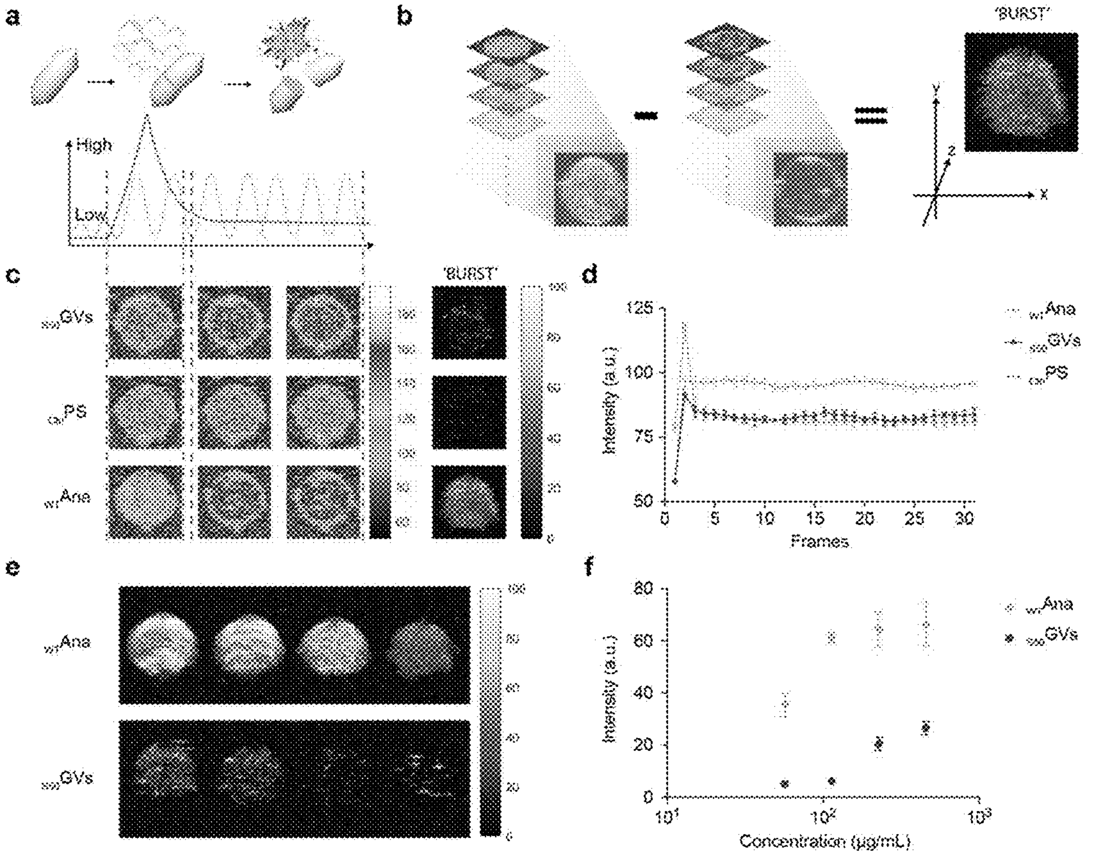
FIGS. 4A-4F show the ultrasound imaging characterization of WTGVs and $_{S50}$GVs.

A recent study introduced the BURST method describing that, during the collapse of GVs under high ultrasound pressure, a high signal intensity can be captured, which in turn provides a sensitive means of imaging GVs down to single-cell sensitivity (Sawyer et al., 2021). To determine whether $_{S50}$GV can generate ultrasound signals and quantitively measure how much ultrasound signal can be generated compared to their larger counterparts such as microbubbles and WTAna GVs, the high-intensity signals during the collapse of $_{S50}$GVs were captured according to the above-mentioned BURST method while employing focused ultrasound in conventional linear array B-mode imaging (FIG. 4A). Compared to the plane-wave imaging used in the BURST method, B-mode imaging was employed here to ensure the effective collapse of $_{S50}$GVs by the 21 MHz transducer. A series of 30 frames were recorded to capture the collapse process. The frames were divided into two groups: the first 15 frames as the 'signal' group and the last 15 frames as the 'background' group. The BURST signal was filtered out by employing max-intensity projection followed by subtraction (FIG. 4B). Under this imaging scheme, normal biological tissues and non-collapsable ultrasound contrast agents such as polystyrene beads would not produce a difference pre- and post-treatment of high-intensity acoustic pressure. Indeed, when $_{S50}$GVs, $_{WT}$Ana GVs and polystyrene beads ($_{Ctrl}$PS) were loaded into an agarose phantom, strong signals were observed in the first few frames of the series from both GV types and the signal decreased rapidly; in comparison, $_{Ctrl}$PS showed a strong signal but was unaltered throughout the series. Thus, after subtraction, only the two GV types showed 'BURST' signals (FIG. 4C). Tracking the intensity frame-by-frame showed a clear 'BURST' peak for both $_{S50}$GV and $_{WT}$Ana GVs (FIG. 4D). Thus, without being bound by theory, $_{S50}$GVs behave similarly to wildtype GVs and microbubbles, and methods such as BURST are suitable and ideal for $_{S50}$GVs.

A concentration series of $_{S50}$GVs and $_{WT}$Ana GVs was constructed to quantitatively determine their ultrasound contrast. These GVs were loaded into an agarose phantom, and the results showed that both $_{S50}$GVs and $_{WT}$Ana GVs displayed clear concentration-dependent signals (FIG. 4E). At the same protein concentration of $_{S50}$GVs and $_{WT}$Ana GVs, $_{WT}$Ana produced a much stronger signal (FIG. 4F). This is expected because, when the diameter of GVs decreases, as in the case of $_{S50}$GVs, and the shell protein thickness remains constant, the gas-to-protein ratio will decrease, resulting in a smaller amount of air and less contrast at a given quantity of proteins (Table 1). The ultrasound contrast of $_{S50}$GVs, quantitatively established according to the above description and illustrated in FIG. 4, will, without being bound by theory, serve as a guideline for their usage in contrast-enhanced ultrasound imaging and molecular imaging of biomarkers.

F. Materials and Methods i Cloning, Expression, and Purification of GVs

Plasmids pST39-pNL29 and ARG1 were obtained from Addgene to encode GV gene clusters from *B. megaterium* and gvpA from *A. flos-aquae*, respectively (#91696 and #106473), and from these two plasmids, the genetic sequence of the major shell protein of $_{S50}$GVs was constructed using Q5 DNA polymerase and Gibson assembly kits (New England Biolabs Inc.) (Gibson et al., 2009). To express $_{S50}$GVs and $_{WT}$Mega GVs, the plasmids were transformed into BL21 Star™ (DE3) pLysS One Shot™ *E. coli* strain and cultured in LB Miller Broth (Thermo Fisher Scientific, Waltham, MA) with 100 μg/mL Carbenicillin (Gold Biotechnology, Olivette, MO), 25 μg/mL Chloramphenicol (MilliporeSigma, Burlington, MA), and 0.2% glucose (MilliporeSigma, Burlington, MA). The cells were induced with 80 μM Isopropyl β-d-1-thiogalactopyranoside (IPTG) (Teknova, Hollister, CA) for 22 hrs at 28.5° C. After reaching an OD600 of 0.6, cells were collected and pelleted by centrifugation at 400×g in 50 mL conical tubes, and then the middle layer was removed to isolate the remaining cells. The cells were mixed with SoluLyse-Tris and lysozyme (Genlantis, San Diego, CA) and DNase I (MilliporeSigma, Burlington, MA), and the lysate was transferred to 2 mL tubes for the three cycles of centrifugally assisted flotation. To uncluster the $_{S50}$GVs and $_{WT}$Mega GVs, the solution was mixed with urea to a final concentration of 6 M, followed by gentle agitation at room temperature for 1 hour as previously described (Lakshmanan et al., 2017). The resulting solution was then stored at 4° C. until the time of usage. After this period, the GV solution was resuspended in 1×PBS and centrifuged at 350×g for overnight at 4° C. This process was repeated 3 times to ensure the complete removal of bottom urea media. This process usually results in a substantial reduction in the optical density at 500 nm (OD500) of the GVs and thus the $_{S50}$GVs referenced in the paper were measured after the unclustering procedure. To produce $_{WT}$Ana GVs, *A. flos-aquae* (CCAP strain 1403/13 F) was cultured and harvested as previously described (Lakshmanan et al., 2017). The floating cells were lysed using sorbitol and Solulyse solution (Genlantis), and GVs were separated from debris through repeated centrifugally assisted flotation.

ii Hydrodynamic Size Measurement

To measure the hydrodynamic diameter of clustered and un-clustered GVs, purified GV samples were diluted to $OD_{500}$=0.2 in 1×PBS and 500 μL of each sample was transferred into a cuvette (Thermo Fisher Scientific, Waltham, MA). The measurements were taken using a Malvern Zen 3600 Zetasizer (Malvern, UK) with a minimum of three measurements per sample. At least three biological replicates were conducted for each type of GV.

iii Transmission Electron Microscopy

To prepare the lymph tissue samples for TEM, extracted tissue was fixed overnight at room temperature in Karnovsky's fixative (Electron Microscopy Sciences, Hatfield, PA) and then post-fixed for one hour in 1% osmium tetroxide. Samples were dehydrated in a graded series of ethanol, embedded in epoxy resin and polymerized overnight at 70° C. Ultra-thin sections of 100 nm thickness were cut using an ultramicrotome (Leica EM UC7), placed on an unsupported 200-mesh copper grid, and then post-stained with saturated methanolic uranyl acetate and Reynold's lead citrate. Images were collected using a JEOL JEM-1400Flash TEM operating at 120 kV and equipped with an AMT NanoSprint15 sCMOS sensor. For TEM of negatively stained purified GVs, samples were diluted to $OD_{500}$=0.2 in 1×PBS and loaded onto 200-mesh carbon-coated copper grids (Ted Pella, Redding, CA) for three minutes. Excess liquid was carefully blotted away with filter paper, and the samples were then stained with 2% (w/v) uranyl acetate (Electron Microscopy Sciences, Hatfield, PA). High-resolution TEM images were captured using a JEOL JEM-2010 TEM and a JEOL JEM-2100F TEM.

iv Fluorescence Live Animal Imaging

To monitor the migration of GVs to the lymphatic system, GVs and 50 nm amine gold nanoparticles were first labeled with NHS-Alexa488 (Thermo Fisher Scientific, Waltham, MA). These fluorescently labeled GVs and gold nanoparticles was then dissolved in 20 μL of PBS under sterilized condition. Following previously described procedures (Harrell et al., 2007; Proulx et al., 2013; Zeng et al., 2017) prepared solutions were injected directly into the interstitial space of the BALB/c mouse paw (N=3 per group) to allow the uptake into the lymphatic system. The animals were imaged at 60 and 90 minutes post-injection using IVIS Lumina II (Advanced Molecular Vision) following the manufacturer's recommended procedures and settings. To analyze lymph node accumulation, the intensity of the axillary lymph node was measured using a region of interest (ROI) within the representative area. The lymph node's relative intensity was calculated as the ratio of the lymph node intensity to the primary injection site intensity, i.e., relative intensity=(lymph node intensity)/(primary injection site intensity). All mice were euthanized when the targeted axillary lymph node reached a similar relative intensity (~0.9), and then the axillary lymph node was dissected for further analysis. For $_{WT}$Ana group two different samples were collected (both 60 min and 90 min). All animal procedures were approved by the Institutional Animal Care and Use Committee (IACUC) of Rice University and performed according to the guidelines.

v Immunohistology

To further analyze the dissected lymph node tissues from all experimental groups, including $_{S50}$GV, $_{WT}$Ana GVs, and 50 nm gold nanoparticles, the lymph node tissues were fixed with 4% paraformaldehyde and sectioned into 15 μm slides Immunohistochemistry was performed to evaluate the expression of specific markers, LYVE-1 and CD45. The slides were first blocked for 1 hour with 5% goat serum (MP Biomedicals, California) in a washing solution consisting of 0.5% Triton X-100 in 1×PBS. The primary antibodies used in this study were LYVE-1 (E3L3V) Rabbit mAb (cat. no. 67538S, Cell Signaling, Danvers, MA) and CD45 (30-F11) Rat mAb (cat. no. 55307S, Cell Signaling, Danvers, MA). The antibodies were diluted 1:200 in 5% goat serum and incubated overnight at 4° C. Following incubation, the slides were washed three times with the washing solution for 5 minutes each. The secondary antibodies, Anti-rat IgG (H+L), Alexa Fluor 647 (cat. no. 4418, Cell Signaling, Danvers, MA) and Anti-rabbit IgG (H+L) Alexa Fluor 350 (cat. no. 11046, Invitrogen, Waltham, Massachusetts) were diluted 1:200 in 1×PBS. The slides were then incubated with the secondary antibodies for 1 hour at room temperature. The images were acquired using a Nikon A1R-si Laser Scanning Confocal Microscope (Japan), equipped with a laser of 405/488/561/638 nm. The expression of LYVE-1 and CD45 in the tissue was evaluated by examining the staining pattern of each antibody within the lymph node tissue samples.

vi Ultrasound Imaging

The imaging phantoms were fabricated by preparing a 1% agarose solution in PBS. Various concentrations of GVs in PBS were mixed with a PBS solution containing 2% agarose in a 1:1 ratio at 50° C., immediately followed by loading 150 μL of the resultant mixture into wells in the phantom. The imaging was performed using a Vevo F2 system (FUJIFILM Visualsonics Inc., Toronto, Canada), equipped with an ultrasound probe of central transmit frequency of 21 MHz (UHF29x). All images were taken with the VADA interface using customized sequences and processed using MATLAB. The B-mode BURST sequence consists of a single low-pressure frame (11% output power at the VADA interface) and 30 high-pressure frames (75% output power), each with 5 focused points. Thus, a total of 151 frames were acquired in each series. The five focal point frames were first combined, and the resulting 30 high-pressure frames were divided into two groups: the initial 15 high-pressure frames were considered as the 'signal' group, while the remaining 15 frames were regarded as the 'background' group. A single frame of 'signal' and 'background' was formed using maximum intensity projection of the 15 frames. The final BURST image was generated by pixel-wise subtraction of the 'background' from the 'signal'.

vii Quantification and Statistical Analysis

Information on sample size (n) and P-values for the experiments can be found in the figures, figure captions, and method section. Statistical analysis was performed using GraphPad Prism software and presented as mean±standard deviation (StdDev). Multiple comparisons were analyzed using Welch and Brown-Forsythe ANOVA tests, which do not assume equal variances across all groups in a population. Significance was set at $p<0.05$.

REFERENCES

The following references, to the extent that they provide exemplary procedural or other details supplementary to those set forth herein, are specifically incorporated herein by reference:

Arvanitis, C. D., Ferraro, G. B., and Jain, R. K. (2020). The blood-brain barrier and blood-tumour barrier in brain tumours and metastases. Nature Reviews Cancer 20, 26-41.

Banks, W. A. (2016). From blood-brain barrier to blood-brain interface: new opportunities for CNS drug delivery. Nature Reviews Drug Discovery 15, 275-292.

Bar-On, Y. M., Flamholz, A., Phillips, R., and Milo, R. (2020). SARS-CoV-2 (COVID-19) by the numbers. eLife 9, e57309.

Bez, M., Foiret, J., Shapiro, G., Pelled, G., Ferrara, K. W., and Gazit, D. (2019). Nonviral ultrasound-mediated gene delivery in small and large animal models. Nat Protoc 14, 1015-1026.

Bez, M., Sheyn, D., Tawackoli, W., Avalos, P., Shapiro, G., Giaconi, J. C., Da, X., David, S. B., Gavrity, J., Awad, H. A., et al. (2017). In situ bone tissue engineering via ultrasound-mediated gene delivery to endogenous progenitor cells in mini-pigs. Sci Transl Med 9, eaal3128.

Brennen, C. E. (1995). Cavitation and bubble dynamics (Cambridge university press).

Chen, S., Ding, J.-h., Bekeredjian, R., Yang, B.-z., Shohet, R. V., Johnston, S. A., Hohmeier, H. E., Newgard, C. B., and Grayburn, P. A. (2006). Efficient gene delivery to pancreatic islets with ultrasonic microbubble destruction technology. Proc Natl Acad Sci USA 103, 8469-8474.

Farhadi, A., Ho, G., Kunth, M., Ling, B., Lakshmanan, A., Lu, G., Bourdeau, R. W., Schröder, L., and Shapiro, M. G. (2018). Recombinantly expressed gas vesicles as nanoscale contrast agents for ultrasound and hyperpolarized MRI. AIChE Journal 64, 2927-2933.

Ferrara, K., Pollard, R., and Borden, M. (2007). Ultrasound microbubble contrast agents: fundamentals and application to gene and drug delivery. Annu Rev Biomed Eng 9, 415-447.

Fujii, H., Li, S.-H., Wu, J., Miyagi, Y., Yau, T. M., Rakowski, H., Egashira, K., Guo, J., Weisel, R. D., and Li, R.-K. (2011). Repeated and targeted transfer of angiogenic plasmids into the infarcted rat heart via ultrasound targeted microbubble destruction enhances cardiac repair. Eur Heart J 32, 2075-2084.

Gaumet, M., Vargas, A., Gurny, R., and Delie, F. (2008). Nanoparticles for drug delivery: The need for precision in reporting particle size parameters. Eur J Pharm Biopharm 69, 1-9.

Gibson, D. G., Young, L., Chuang, R.-Y., Venter, J. C., Hutchison, C. A., and Smith, H. O. (2009). Enzymatic assembly of DNA molecules up to several hundred kilobases. Nat Methods 6, 343-345.

Harrell, M. I., Iritani, B. M., and Ruddell, A. (2007). Tumor-induced sentinel lymph node lymphangiogenesis and increased lymph flow precede melanoma metastasis. The American journal of pathology 170, 774-786.

Ilovitsh, T., Feng, Y., Foiret, J., Kheirolomoom, A., Zhang, H., Ingham, E. S., Ilovitsh, A., Tumbale, S. K., Fite, B. Z., Wu, B., et al. (2020). Low-frequency ultrasound-mediated cytokine transfection enhances T cell recruitment at local and distant tumor sites. Proc Natl Acad Sci USA 117, 12674-12685.

Irvine, D. J., and Dane, E. L. (2020). Enhancing cancer immunotherapy with nanomedicine. Nature Reviews Immunology 20, 321-334.

Jafari Sojahrood, A., de Leon, A. C., Lee, R., Cooley, M., Abenojar, E. C., Kolios, M. C., and Exner, A. A. (2021). Toward Precisely Controllable Acoustic Response of Shell-Stabilized Nanobubbles: High Yield and Narrow Dispersity. ACS Nano 15, 4901-4915.

Janib, S. M., Moses, A. S., and MacKay, J. A. (2010). Imaging and drug delivery using theranostic nanoparticles. Adv Drug Del Rev 62, 1052-1063.

Khestanova, E., Guinea, F., Fumagalli, L., Geim, A. K., and Grigorieva, I. V. (2016). Universal shape and pressure inside bubbles appearing in van der Waals heterostructures. Nature Communications 7, 12587.

Lakshmanan, A., Lu, G. J., Farhadi, A., Nety, S. P., Kunth, M., Lee-Gosselin, A., Maresca, D., Bourdeau, R. W., Yin, M., Yan, J., et al. (2017). Preparation of biogenic gas vesicle nanostructures for use as contrast agents for ultrasound and MRI. Nat Protoc 12, 2050-2080.

Li, Z., Shen, Q., Dai, Y., Anderson, A. P., Iburg, M., Lin, R., Zimmer, B., Meyer, M. D., You, L., Chilkoti, A., et al. (2023). Spatial organization of gas vesicles is governed by phase-separable GvpU. under review.

Lindner, J. R. (2004). Microbubbles in medical imaging: current applications and future directions. Nature Reviews Drug Discovery 3, 527-533.

Mitragotri, S. (2005). Healing sound: the use of ultrasound in drug delivery and other therapeutic applications. Nature Reviews Drug Discovery 4, 255-260.

Pfeifer, F. (2012). Distribution, formation and regulation of gas vesicles. Nat Rev Microbiol 10, 705-715.

Pfeifer, F. Recent Advances in the Study of Gas Vesicle Proteins and Application of Gas Vesicles in Biomedical Research. Life 2022, 12, 1455.

Proulx, S. T., Luciani, P., Christiansen, A., Karaman, S., Blum, K. S., Rinderknecht, M., Leroux, J.-C., and Detmar, M. (2013). Use of a PEG-conjugated bright near-infrared dye for functional imaging of rerouting of tumor lymphatic drainage after sentinel lymph node metastasis. Biomaterials 34, 5128-5137.

Sawyer, D. P., Bar-Zion, A., Farhadi, A., Shivaei, S., Ling, B., Lee-Gosselin, A., and Shapiro, M. G. (2021). Ultrasensitive ultrasound imaging of gene expression with signal unmixing. Nat Methods 18, 945-952.

Schudel, A., Francis, D. M., and Thomas, S. N. (2019). Material design for lymph node drug delivery. Nature Reviews Materials 4, 415-428.

Shapiro, M. G., Goodwill, P. W., Neogy, A., Yin, M., Foster, F. S., Schaffer, D. V., and Conolly, S. M. (2014). Biogenic gas nanostructures as ultrasonic molecular reporters. Nat Nanotechnol 9, 311-316.

Shimamura, M., Sato, N., Taniyama, Y., Yamamoto, S., Endoh, M., Kurinami, H., Aoki, M., Ogihara, T., Kaneda, Y., and Morishita, R. (2004). Development of efficient plasmid DNA transfer into adult rat central nervous system using microbubble-enhanced ultrasound. Gene Ther 11, 1532-1539.

Sirsi, S. R., and Borden, M. A. (2009). Microbubble compositions, properties and biomedical applications. Bubble Science, Engineering & Technology 1, 3-17.

Swartz, M. A. (2001). The physiology of the lymphatic system. Adv Drug Del Rev 50, 3-20.

Takeuchi, D., Sato, N., Shimamura, M., Kurinami, H., Takeda, S., Shinohara, M., Suzuki, S., Kojima, M., Ogihara, T., and Morishita, R. (2008). Alleviation of AP-induced cognitive impairment by ultrasound-mediated gene transfer of HGF in a mouse model. Gene Ther 15, 561-571.

Terstappen, G. C., Meyer, A. H., Bell, R. D., and Zhang, W. (2021). Strategies for delivering therapeutics across the blood-brain barrier. Nature Reviews Drug Discovery 20, 362-383.

Walsby, A. E. (1994). Gas vesicles. Microbiol Rev 58, 94-144.

Walsby, A. E., Revsbech, N. P., and Griffel, D. H. (1992). The gas permeability coefficient of the cyanobacterial gas vesicle wall. Microbiology 138, 837-845.

Zeng, Q., Li, H., Jiang, H., Yu, J., Wang, Y., Ke, H., Gong, T., Zhang, Z., and Sun, X. (2017). Tailoring polymeric hybrid micelles with lymph node targeting ability to improve the potency of cancer vaccines. Biomaterials 122, 105-113.

Zolochevska, O., Xia, X., Williams, B. J., Ramsay, A., Li, S., and Figueiredo, M. L. (2011). Sonoporation Delivery of Interleukin-27 Gene Therapy Efficiently Reduces Prostate Tumor Cell Growth In Vivo. Hum Gene Ther 22, 1537-1550.

What is claimed:

1. A gas vesicle composition comprising:

(A) a modified shell protein, wherein the amino acid sequence of the modified shell protein comprises a first fragment and a second fragment, wherein:

(i) the first fragment comprises SEQ ID NO: 1; and (ii) the second fragment comprises SEQ ID NO: 2; and (B) at least one gas vesicle assembly protein selected from the group consisting of *Bacillus megaterium* gvpR, *Bacillus megaterium* gvpN, *Bacillus megaterium* gvpF, *Bacillus megaterium* gvpG, *Bacillus megaterium* gvpL, *Bacillus megaterium* gvpS, *Bacillus megaterium* gvpK, *Bacillus megaterium* gvpJ, *Bacillus megaterium* gvpT, *Bacillus megaterium* gvpU, *Anabaena flos-aquae* gvpN, *Anabaena flos-aquae* gvpJ, *Anabaena flos-aquae* gvpK, *Anabaena flos-aquae* gvpF, *Anabaena flos-aquae* gvpG, *Anabaena flos-aquae* gvpV, and *Anabaena flos-aquae* gvpW.

2. The gas vesicle composition of claim 1, wherein the at least one gas vesicle assembly protein is selected from the group consisting of *Bacillus megaterium* gvpR, *Bacillus megaterium* gvpN, *Bacillus megaterium* gvpF, *Bacillus megaterium* gvpG, *Bacillus megaterium* gvpL, *Bacillus megaterium* gvpS, *Bacillus megaterium* gvpK, *Bacillus megaterium* gvpJ, *Bacillus megaterium* gvpT, and *Bacillus megaterium* gvpU.

3. The gas vesicle composition of claim 1, wherein the at least one gas vesicle assembly protein is selected from the group consisting of *Anabaena flos-aquae* gvpN, *Anabaena flos-aquae* gvpJ, *Anabaena flos-aquae* gvpK, *Anabaena flos-aquae* gvpF, *Anabaena flos-aquae* gvpG, *Anabaenaflos-aquae* gvpV, and *Anabaenaflos-aquae* gvpW.

4. The gas vesicle composition of claim 1, wherein the composition further comprises at least one additional shell protein.

5. The gas vesicle composition of claim 1, wherein the modified shell protein comprises a fusion protein comprising the first fragment and the second fragment.

6. The gas vesicle composition of claim 1, wherein the first fragment comprises SEQ ID NO: 1, the second fragment comprises SEQ ID NO: 2, and the gas vesicle composition comprises *Bacillus megaterium* gvpR, *Bacillus megaterium* gvpN, *Bacillus megaterium* gvpF, *Bacillus megaterium* gvpG, *Bacillus megaterium* gvpL, *Bacillus megaterium* gvpS, *Bacillus megaterium* gvpK, *Bacillus megaterium* gvpJ, *Bacillus megaterium* gvpT, and *Bacillus megaterium* gvpU.

7. The gas vesicle composition of claim 1, wherein the composition further comprises a therapeutic molecule.

8. A method of treating a disease or disorder comprising administering a gas vesicle composition of claim 1 to a patient in need thereof.

9. The method of claim 8, wherein the disease or disorder is associated with the lymphatic system.

10. The method of claim 8, wherein the disease or disorder is associated with neuronal cells.

11. A fusion protein comprising SEQ ID NO: 1 and SEQ ID NO: 2.

* * * * *

SEQUENCE LISTING

```
Sequence total quantity: 2
SEQ ID NO: 1            moltype = AA  length = 51
FEATURE                 Location/Qualifiers
source                  1..51
                        mol_type = protein
                        organism = Anabaena flosaquae
SEQUENCE: 1
MAVEKTNSSS SLAEVIDRIL DKGIVIDAWV RVSLVGIELL AIEARIVIAS V           51

SEQ ID NO: 2            moltype = AA  length = 37
FEATURE                 Location/Qualifiers
source                  1..37
                        mol_type = protein
                        organism = Bacillus megaterium
SEQUENCE: 2
DTWLRYAEAV GLLRDDVEEN GLPERSNSSE GQPRFSI                           37
```